Figure 1:
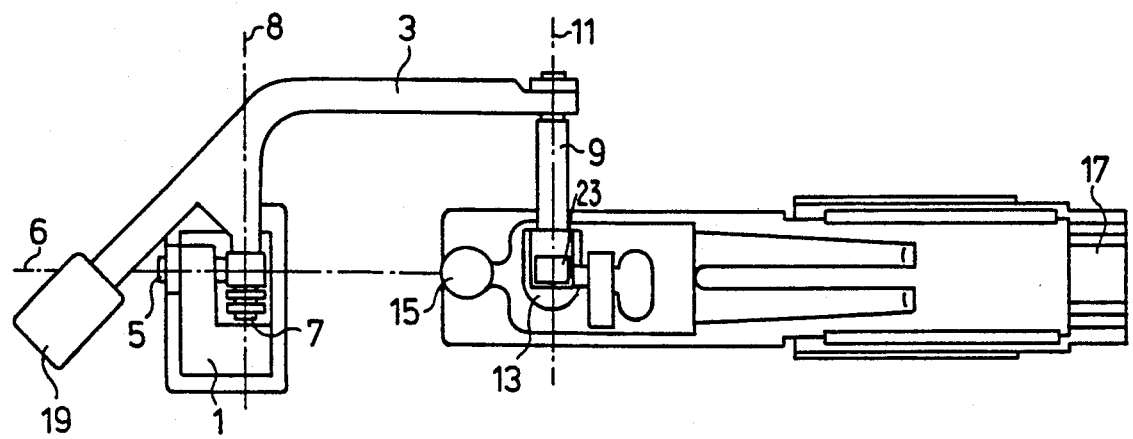

United States Patent [19]

Janssen et al.

[11] Patent Number: 5,040,203
[45] Date of Patent: Aug. 13, 1991

[54] X-RAY EXAMINATION APPARATUS

[75] Inventors: Jozef T. A. Janssen; Johannes G. Van Endschot, both of Eindhoven, Netherlands

[73] Assignee: U.S. Philips Corporation, New York, N.Y.

[21] Appl. No.: 490,118

[22] Filed: Mar. 7, 1990

[30] Foreign Application Priority Data

Mar. 9, 1989 [NL] Netherlands ............... 8900575

[51] Int. Cl.$^5$ .................. H05G 1/02; H05G 1/60
[52] U.S. Cl. ............................ 378/197; 378/193; 378/196; 378/17
[58] Field of Search ............. 378/17, 27, 197, 196, 378/195, 198, 11, 193

[56] References Cited

U.S. PATENT DOCUMENTS

| | | | |
|---|---|---|---|
| 4,481,656 | 11/1984 | Janssen et al. | 378/196 |
| 4,625,226 | 11/1986 | Hanz et al. | 378/19 |
| 4,875,228 | 10/1989 | Archer | 378/197 |
| 4,922,512 | 5/1990 | Lajus et al. | 378/197 |
| 4,987,585 | 1/1991 | Kidd et al. | 378/197 |

FOREIGN PATENT DOCUMENTS

| | | |
|---|---|---|
| 2024037 | 12/1971 | Fed. Rep. of Germany. |
| 2154893 | 6/1972 | Fed. Rep. of Germany. |
| 0155937 | 12/1981 | Japan ............... 378/197 |

Primary Examiner—Edward P. Westin
Assistant Examiner—Don Wong
Attorney, Agent, or Firm—William Squire

[57] ABSTRACT

A simple and robust X-ray stand for angio graphic examinations is obtained by rotatably suspending a U-shaped or C-shaped carrier from an L-shaped arm which is connectd to a vertical column so as to be rotatable about two orthogonal intersecting axes of rotation at the column. The irradiation directions can be readily adjusted by hand when a counterweight is connected to the arm.

12 Claims, 9 Drawing Sheets

X-RAY EXAMINATION APPARATUS

The invention relates to an X-ray examination apparatus, comprising a vertical column whereto there is connected an arm which is rotatable about a horizontal axis and whereto there is connected a carrier which supports at a first end an X-ray source and at a second end an X-ray detector which is arranged opposite the X-ray source.

An X-ray examination apparatus of this kind is known from German Offenlegungsschrift DE 21 54 893.

Of interest is copending application Ser. No. 370,213, filed June 22, 1989, in the name of Van Endschot et al, entitled "X-ray Examination Apparatus Comprising a Balanced Supporting Arm" and assigned to the assignee of the present invention.

The Offenlegungsschrift describes an X-ray apparatus for performing angiographic examinations. For example, cardiac or other blood vessels are irradiated by an X-ray beam emitted by the X-ray source, a projection image of the irradiated objects being detected by the X-ray detector for display. In order to prevent projection distortion and overlapping of details which are interesting from a medical point of view, for example by bone structures, irradiation from a large number of directions is necessary. To this end, the X-ray source and the X-ray detector are arranged opposite one another on a C-shaped carrier which is displaceable along a circular path in a shoe extending along its circumference. An object in the center of the circular path is irradiated from different directions without image translation occurring. In addition to the displacement of the C-shaped carrier along the circular path, the shoe is also capable of rotation so that the plane of the C-shaped carrier is tilted with respect to a vertical position. The enlargement of the object to be displayed is adjustable by variation of the distance between the object and the X-ray detector with respect to the distance between the X-ray source and the object.

The known X-ray examination apparatus has the drawback that the construction is complex and that the apparatus occupies an excessively large part of the space available in an operating room.

It is an object of the invention to provide an X-ray examination apparatus which has a comparatively simple and compact construction and which is suitable for irradiating an object from a plurality of directions. It is also an object of the invention to provide an X-ray examination apparatus in which the irradiation direction can be manually adjusted using only little effort.

To achieve this, an X-ray examination apparatus in accordance with the invention is characterized in that an arm is included for the C-shaped carrier which carrier is also rotatable about an axis of rotation which is rotatable about the horizontal axis and which axis of rotation intersects the horizontal axis at right angles.

When the arm of the present invention is rotated about the horizontal axis, the X-ray source and the X-ray detector on the carrier are rotated together with the carrier about the horizontal axis, a central ray which connects a focus of the X-ray source to the center of the image detector then intersecting the horizontal axis are rotated about the horizontal axis. In the known X-ray apparatus this movement of the central ray is realized by displacement of the C-shaped carrier in a shoe which slides relative to the carrier. An angle between the central ray and the horizontal axis is adjustable by rotation of the carrier about the further axis. In the known X-ray apparatus this angle is adjustable by rotation of the shoe. Rotation of the arm about the axis of rotation enables adjustment of the enlargement of the object to be displayed. Because the central ray is then moved in a direction extending along the horizontal axis, the object will have to perform a translation with respect to the column in order to remain within the X-ray beam. When the distance between the axis of rotation and the central ray is large, the shift of the central ray along the horizontal axis will be negligibly small and the object can remain stationary with respect to the column. In the absence of movement of the X-ray detector with respect to the arm, as necessary for changing the enlargement according to the cited state of the art, the connection of the X-ray detector to the X-ray source can be simple and robust.

An embodiment of an X-ray examination apparatus in accordance with the invention is characterized in that at one end of the arm there is provided a counterweight, the common center of gravity of the arm, the carrier, the X-ray source, the X-ray detector and the counterweight being substantially coincident with the point of intersection of the horizontal axis and the axis of rotation.

Because of the balancing of the X-ray examination apparatus, all positions of the central ray with respect to the object to be displayed can be readily adjusted by hand.

Figure 2:
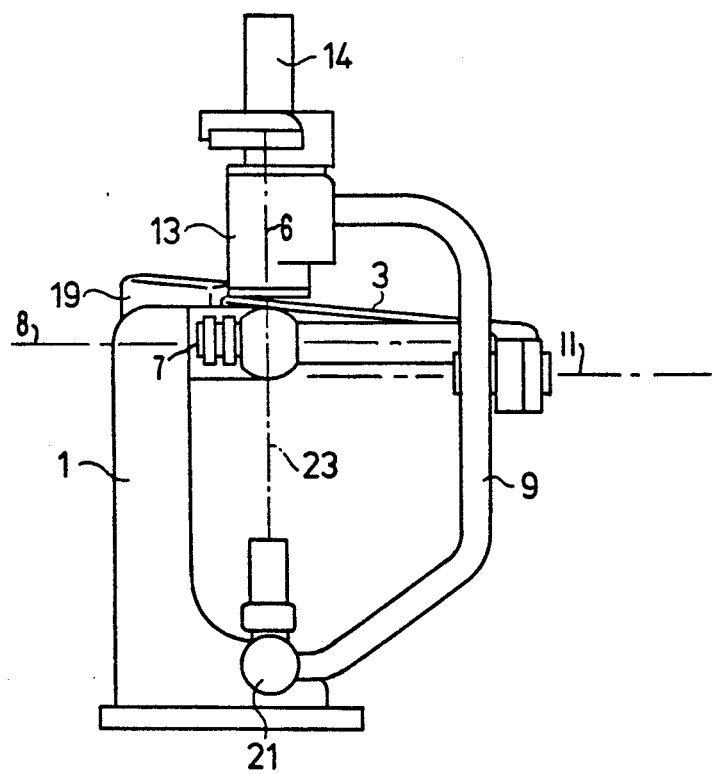
Figure 3A:
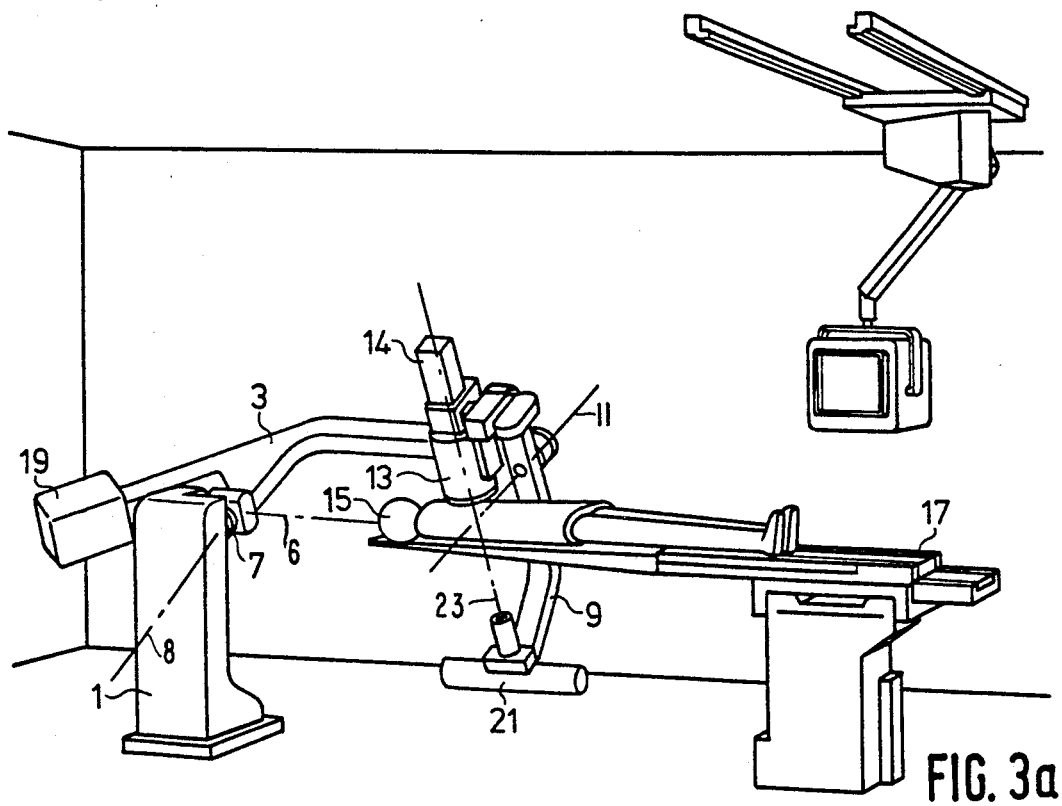
Figure 3B:
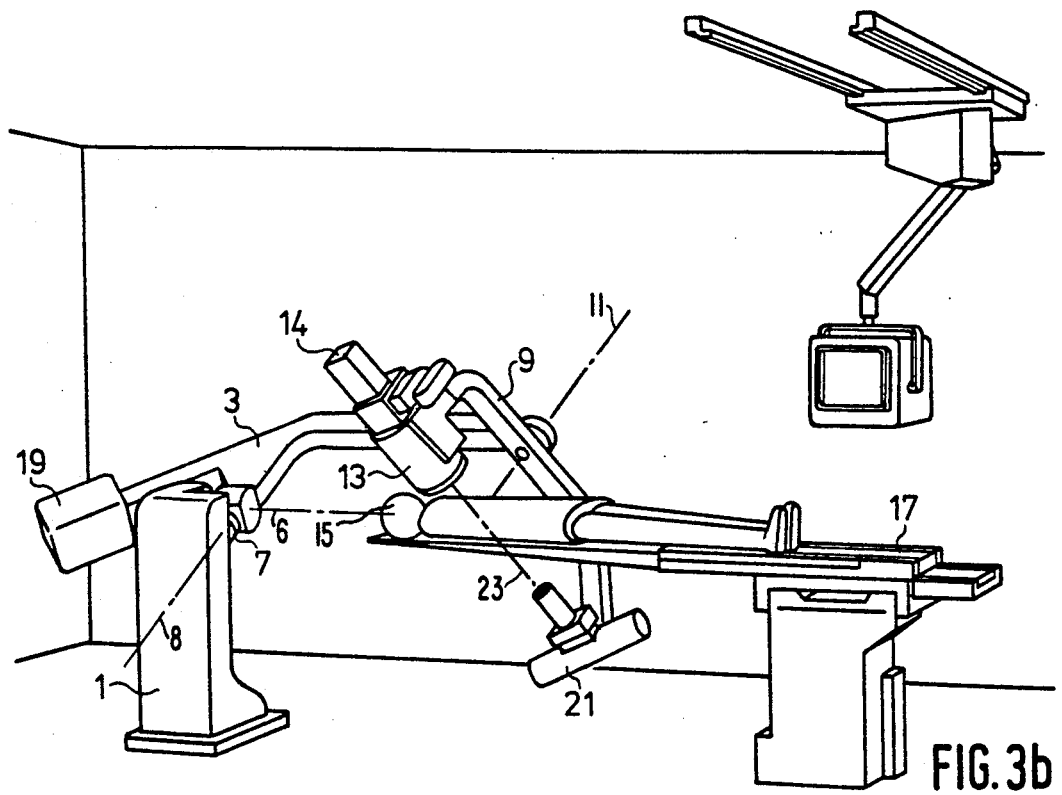
Figure 3C:
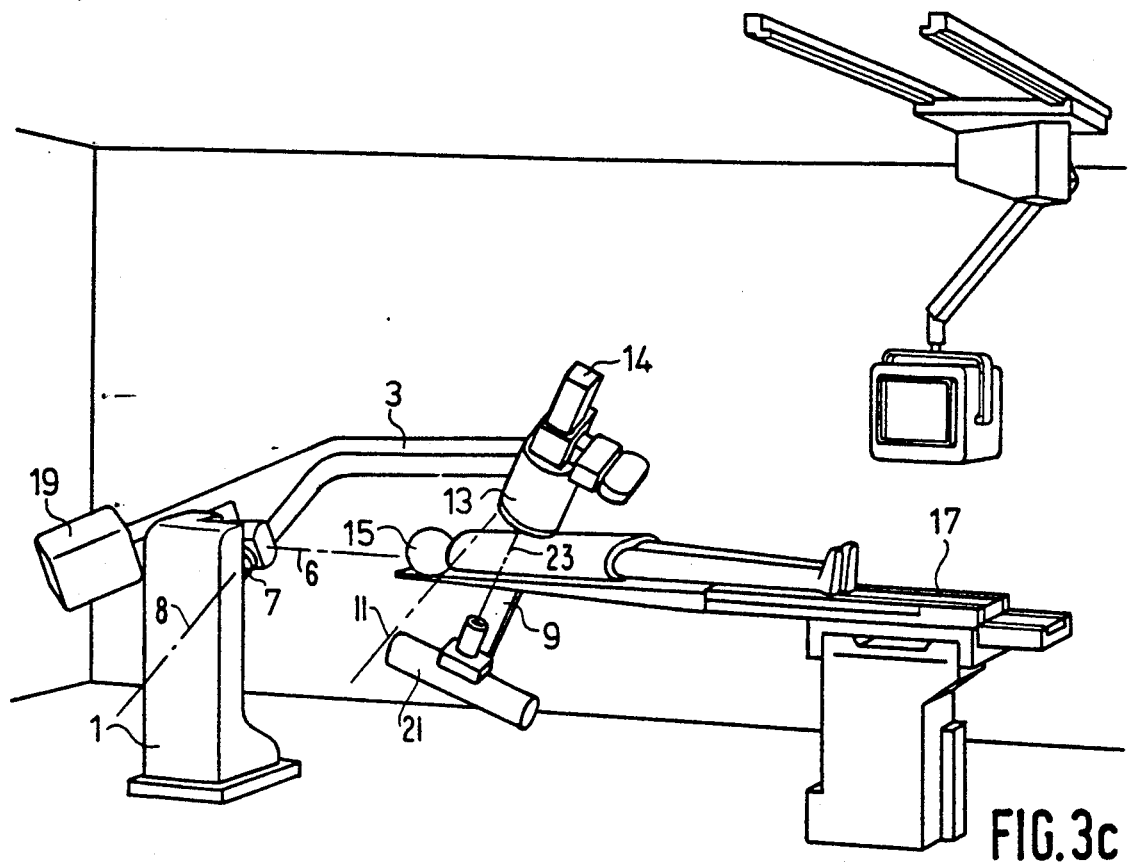
Figure 3D:
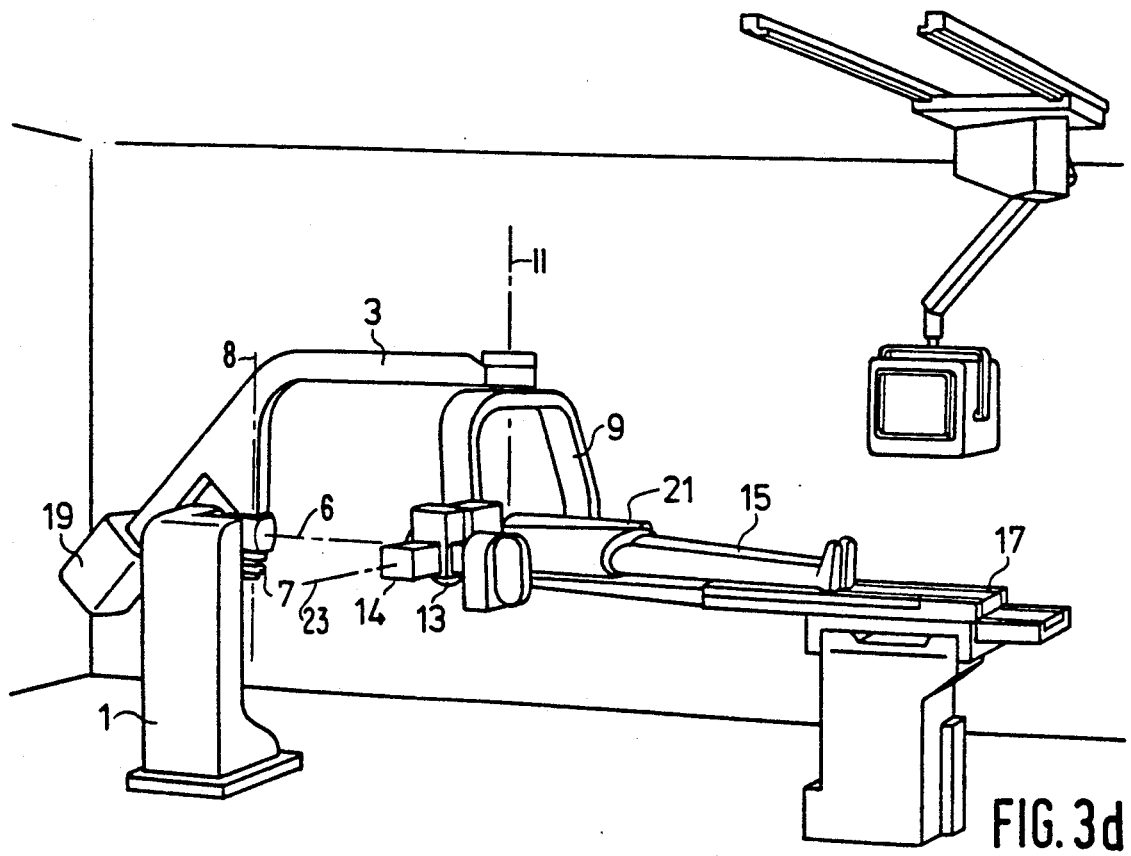
Figure 4A:
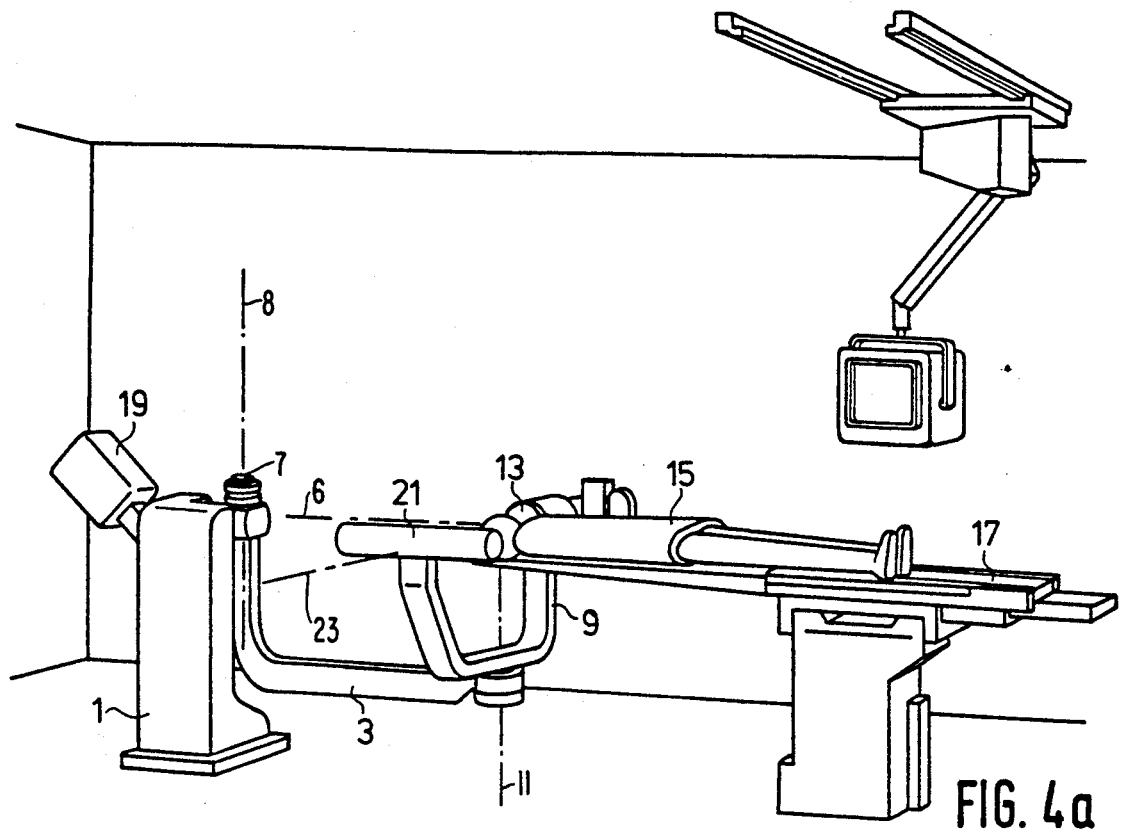
Figure 4B:
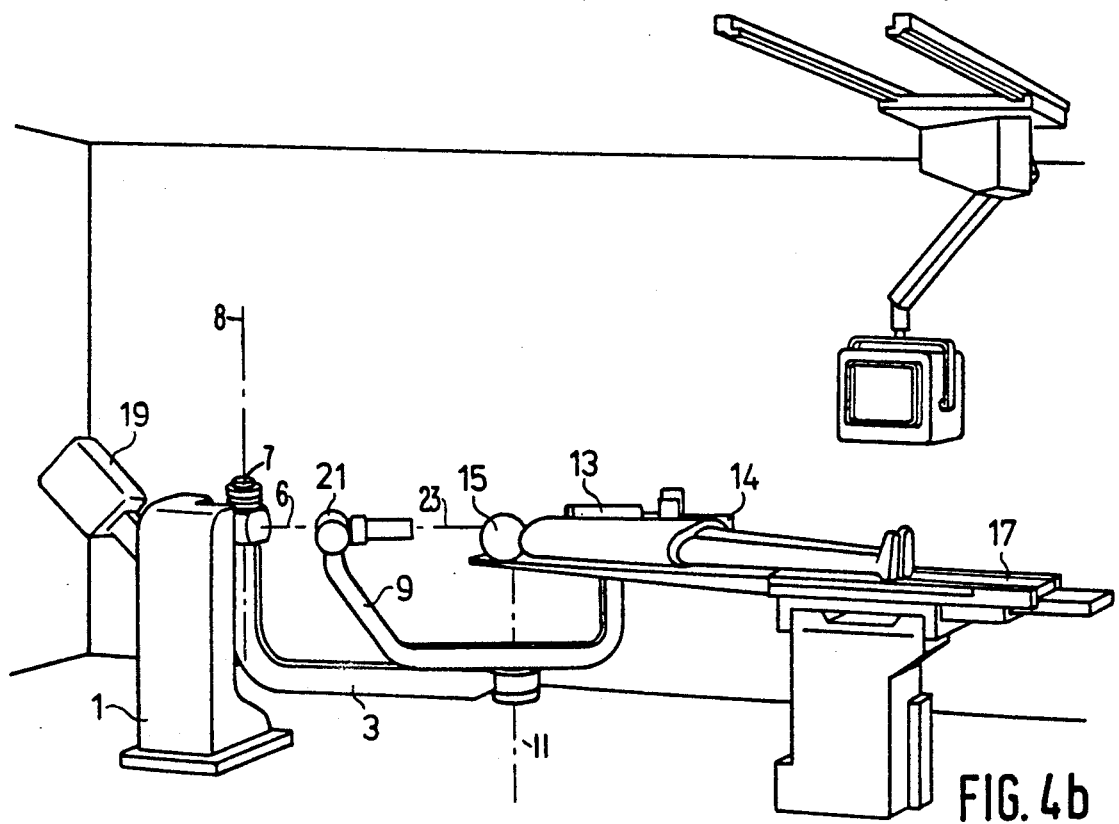
Figure 4C:
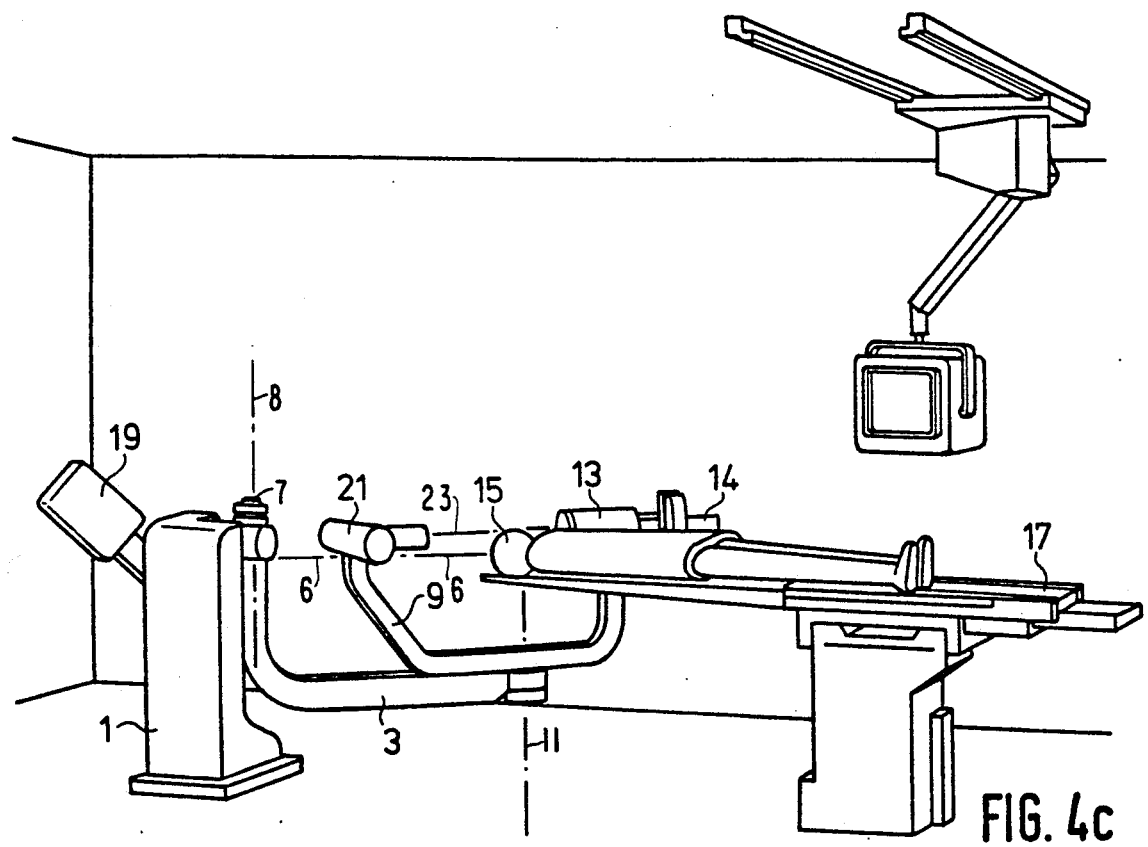
Figure 5A:
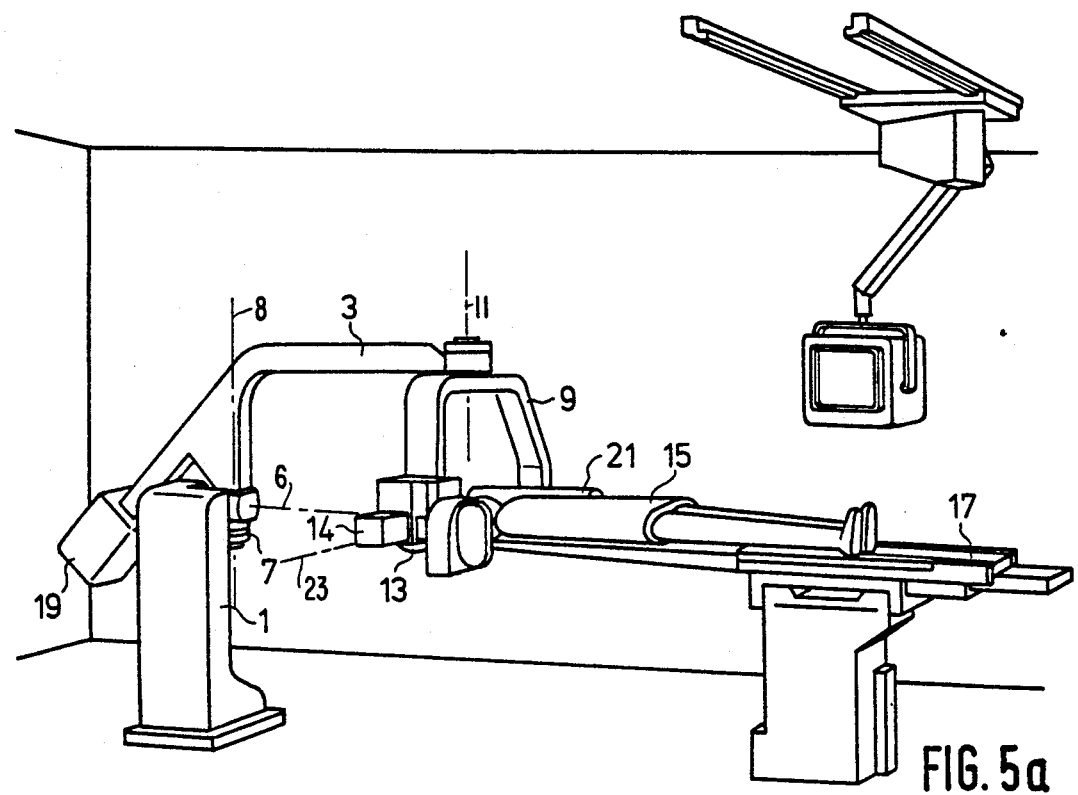
Figure 5B:
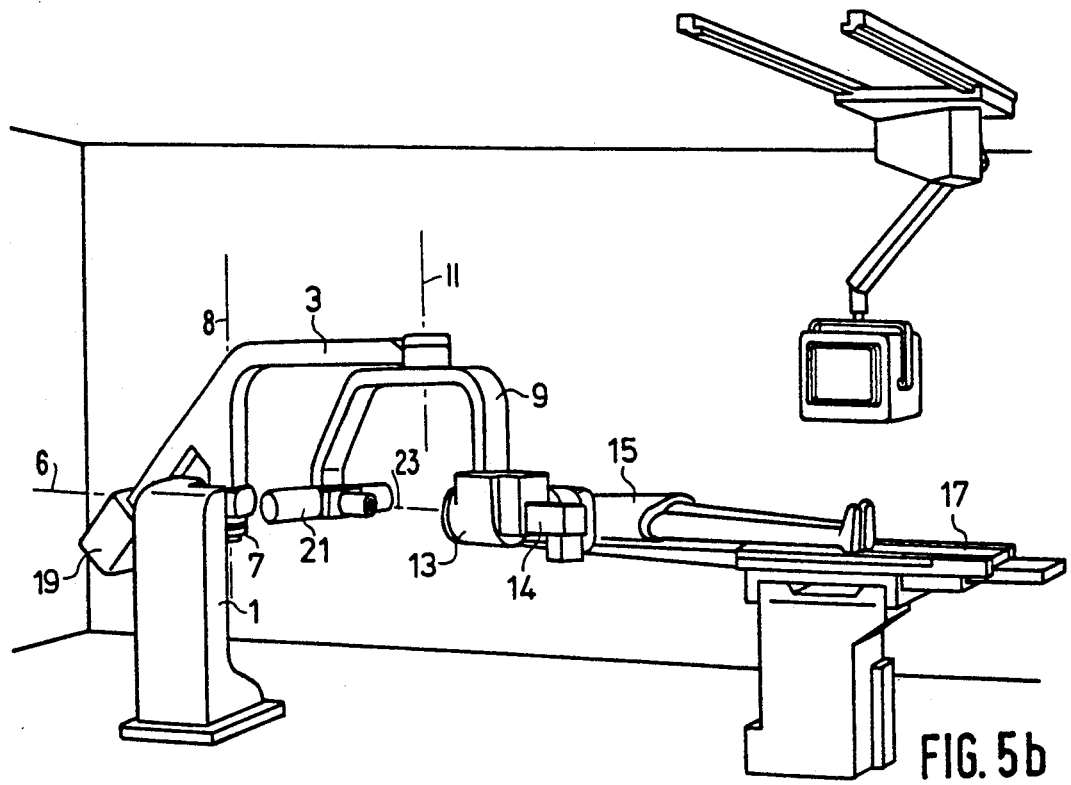
Figure 5C:
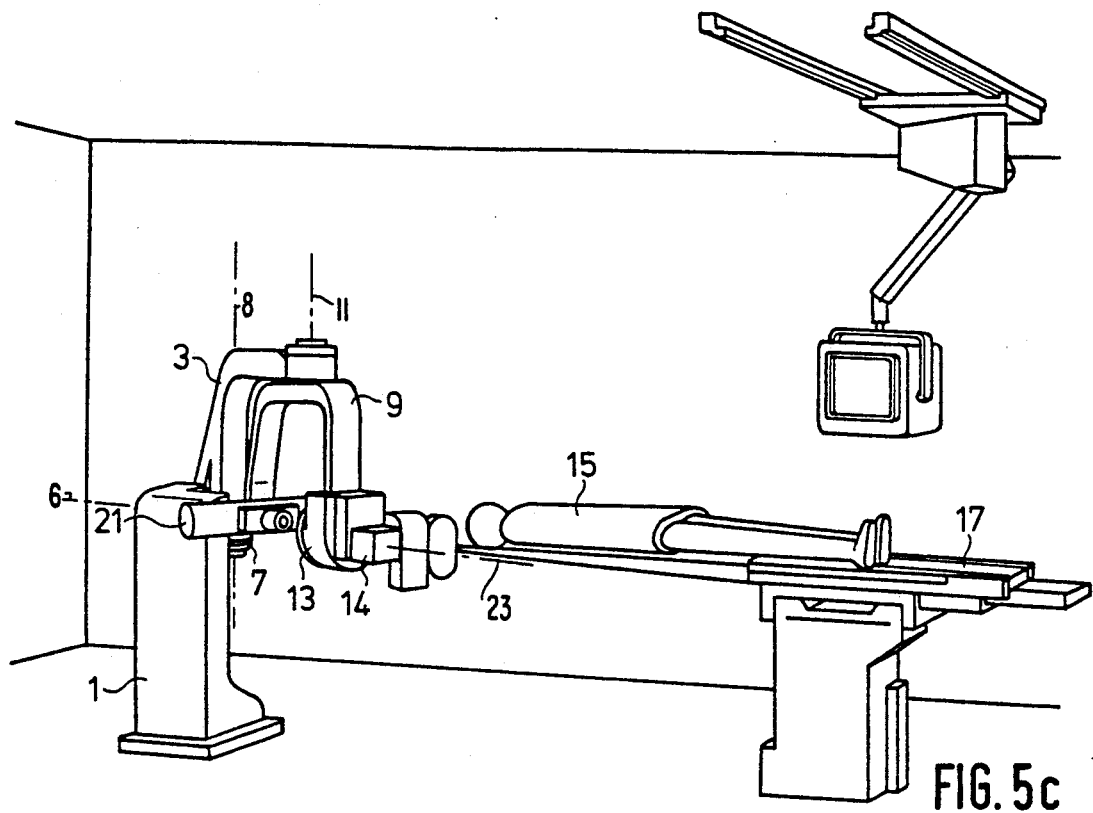
Figure 5D:
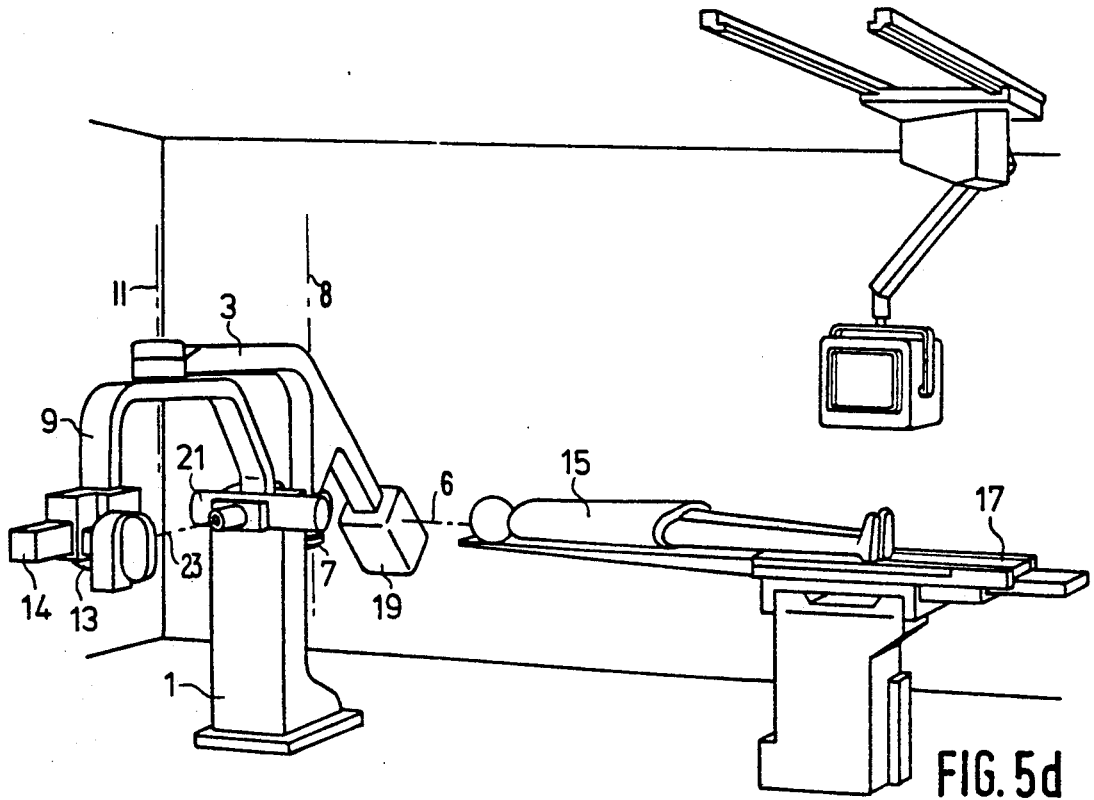
Figure 6A:
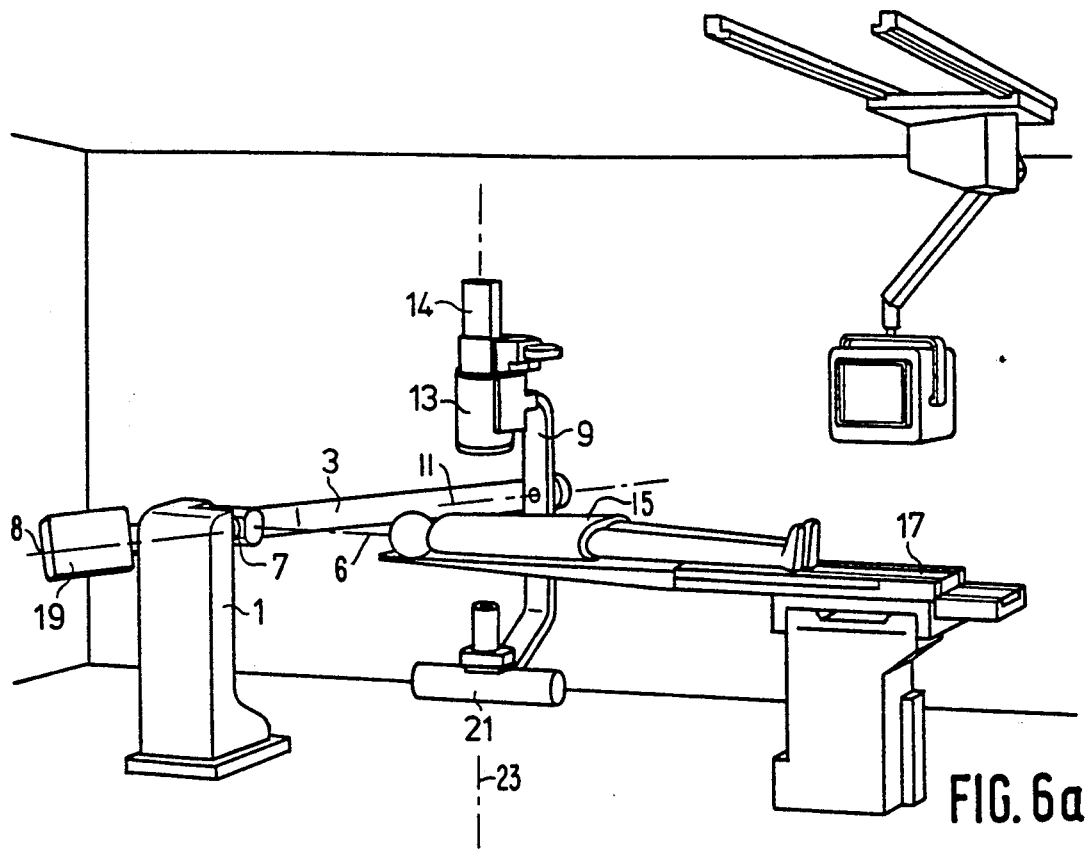
Figure 6B:
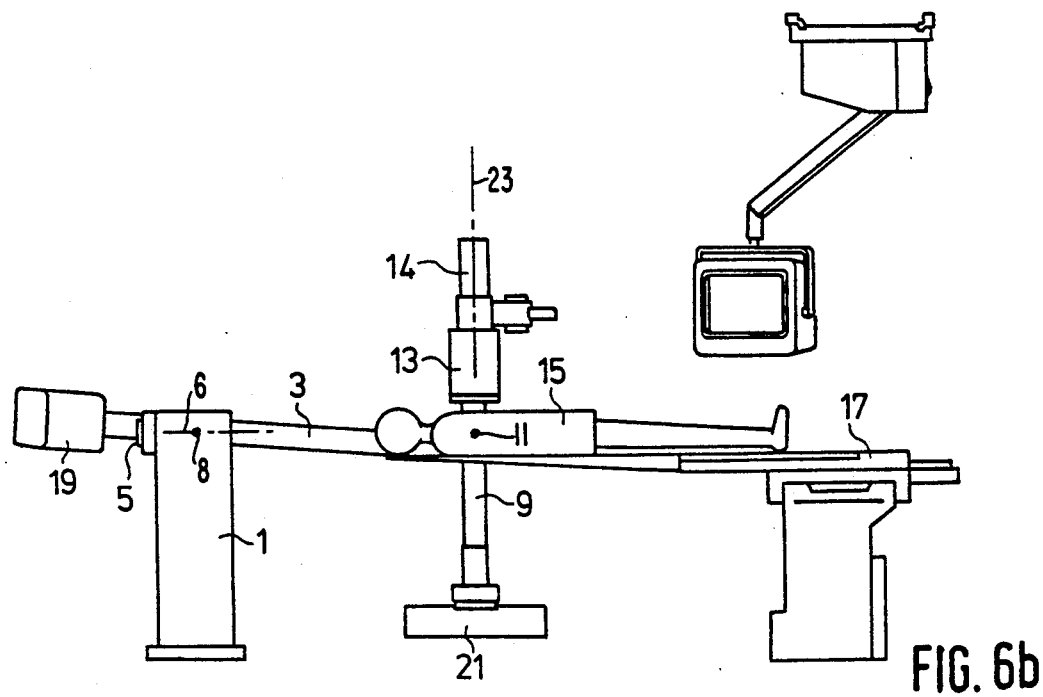
Figure 7:
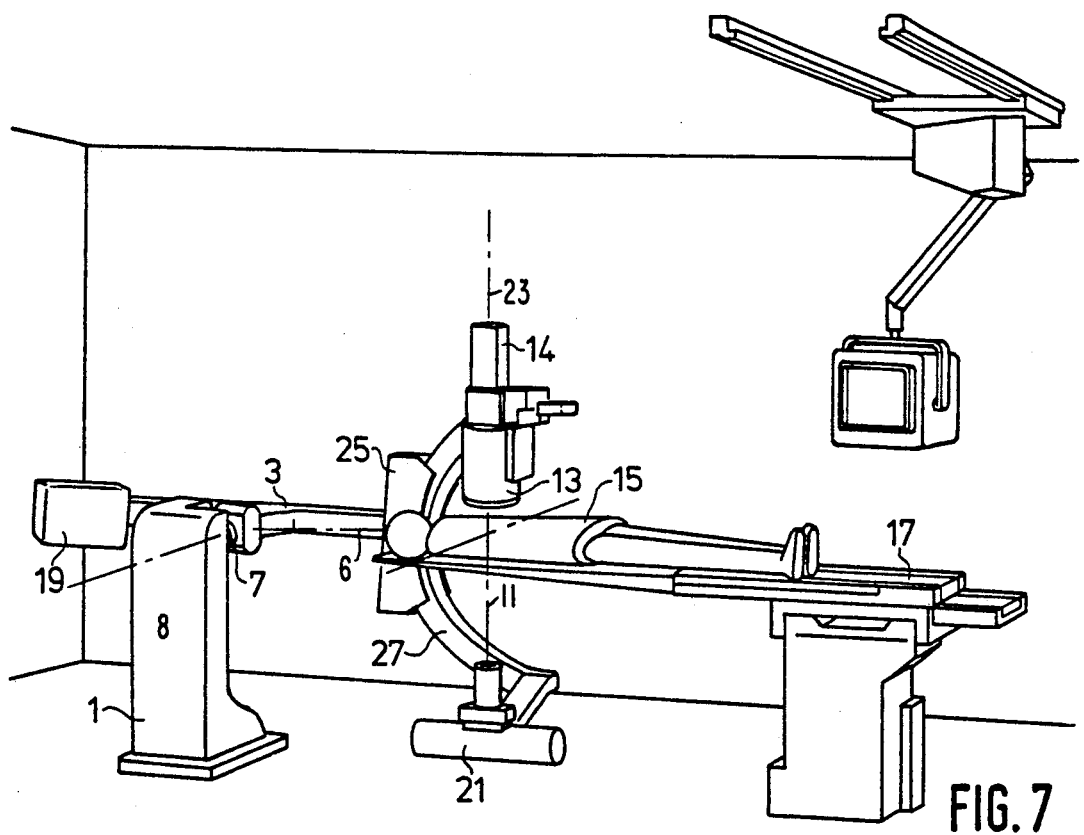

Some embodiments of an X-ray examination apparatus in accordance with the invention will be described in detail hereinafter with reference to the accompanying drawing. Therein:

FIG. 1 is a plan view of an X-ray examination apparatus in accordance with the invention, FIG. 2 is a side elevation of the X-ray examination apparatus, FIGS. 3a–3d show a number of positions of the X-ray examination apparatus in which the axis of rotation of the carrier has been rotated upwards about a horizontal axis, FIGS. 4a–4c show a number of positions of the X-ray examination apparatus in which the axis of rotation of the carrier has been rotated downwards about a horizontal axis, FIGS. 5a–5d illustrate the positioning of the X-ray examination apparatus to a parking position, FIGS. 6a–6b illustrate the adjustment of the enlargement of the image, and FIG. 7 illustrates a method of connecting a C-shaped carrier to the arm.

FIG. 1 shows a column 1 whereto there is connected an arm 3. By way of a spindle 5 the arm 3 is connected to the column 3 so as to be rotatable around the horizontal axis 6. The arm 3 is also rotatable about an axis 8 by way of a spindle 7 which is rotatable about the horizontal axis 6. One end the arm 3 is connected to a C-shaped carrier 9 which is rotatable about a further axis 11. An X-ray image intensifier tube 13 is connected to one end of the carrier 9. A patient 15 is positioned on a table 17 so that the longitudinal direction of the patient extends along the horizontal axis 6. Under the influence of a counterweight 19, the common center of gravity of the image intensifier tube 13, the carrier 9, the arm 3, the X-ray source (not shown in this Figure) and the counterweight 19 is coincident with the point of intersection of the axes 6 and 8.

FIG. 2 shows the column 1, the X-ray image intensifier tube 13, a television camera tube 14 connected to the X-ray image intensifier tube 13, and the X-ray source 21. A central ray 23 interconnects the center of a detection entrance face of the X-ray intensifier tube 13 and the focus of the X-ray source.

FIGS. 3a to 3c show the rotation of the central ray 23 about the axis 6 by rotation of the axis of rotation 8 about the horizontal axis 6. Rotation of the carrier 9 about the axis 11 changes the angle enclosed by the central ray and the axis 6. FIG. 3d shows the position of the carrier 9 when the rotation of the axis 8 about the axis 6 is maximum in one direction.

FIGS. 4a to 4c show the X-ray examination apparatus when the axis 8 is rotated −90° about the axis 6 from the position of FIGS. 1 and 2. For example, for cranovascular examinations the skull can be irradiated in a large number of directions in a horizontal plane.

FIGS. 5a to 5c illustrate how the X-ray examination apparatus can be placed in a parking position by maximum rotation of the axis 8 about the axis 6 to the position of FIG. 3d and subsequent rotation of the arm 3 about axis 8. In the parking position the freedom of movement of, for example, a radiologist around the patient is high and the patient is readily accessible, for example, for transferring the patient from the table to a patient trolley for transport.

The enlargement of the object to be displayed can be adapted by changing the ratio of the distance between the X-ray detector and the object to the distance between the X-ray source and the object, in a horizontal position of the axis 8, by rotating the arm 3 about the axis 8. FIG. 6a shows the X-ray examination apparatus in a position for a large enlargement and FIG. 6b shows the apparatus in a position for a small enlargement. In dependence on the enlargement setting, the patient will have to be displaced in a longitudinal direction, simultaneously with the movement of the arm 3, in order to keep the object to be displayed in the central ray; rotation of the carrier 9 should also take place in order to keep the angle enclosed by the central ray and the axis 6 constant.

FIG. 7 shows one way of connecting a shoe 25 to the arm 3, the shoe accommodating a C-shaped carrier 27. By rotation of the C-shaped carrier 27 in the shoe 25, an object can be irradiated from different sides. In such an embodiment the number of irradiation directions is very large and the image of the object to be displayed is not rotated.

What is claimed is:

1. An X-ray examination apparatus, comprising a column extending in a given direction parallel to the force of gravity, an arm connected to said column and rotatable about a horizontal axis relative to gravity and to which arm there is coupled a carrier which supports at a first end an X-ray source and at a second end an X-ray detector which is arranged opposite the X-ray source, the combination therewith comprising means for rotatably securing the arm to said column for rotation about said horizontal axis and about a second axis rotatable about the horizontal axis, said axes being orthogonal and intersecting, said horizontal axis being normal to said given direction, said means for securing rotatably including a second means for rotatably securing the carrier to said arm for rotation about a further axis which extends parallel to the axis of rotation and spaced from said intersecting axes.

2. An X-ray examination apparatus as claimed in claim 1 including a counterweight secured to the arm at one side in such that the arm, the carrier, the X-ray source, the X-ray detector and the counterweight having a common center of gravity substantially coincident with the point of intersection of the intersecting axes.

3. An X-ray examination apparatus as claimed in claim 2 wherein the carrier is C-shaped, said apparatus including a shoe secured to the carrier and arm such that the carrier is displaceable along a circular path via said shoe.

4. The apparatus as claimed in claim 2, wherein the intersection of said axes is at said column.

5. The apparatus of claim 1 wherein said means for securing the arm to the column comprises a spindle secured to the column for rotation about said horizontal axis and means for securing the arm to the spindle for rotation about the second axis.

6. The apparatus of claim 5 wherein said arm comprises an elongated member including a leg extending at an angle from the member, said leg including said means for securing the arm to the spindle.

7. The apparatus of claim 6 wherein said source and detector define a central X-ray beam axis, said carrier being C-shaped with said beam axis adjacent to the end regions of said carrier, said carrier being rotatably secured to said arm at a region spaced from said spindle, said arm and carrier being dimensioned so that said beam axis intersects said horizontal axis.

8. The apparatus of claim 7 further including counterweight means secured to said arm at an arm region distal the region of the arm to which said carrier is secured for placing the center of gravity of the arm, carrier, source and detector substantially at the intersection of said intersecting horizontal and second axes.

9. An X-ray examination apparatus comprising:
a support;
an arm;
first means rotatably secured to said support for rotation about a first axis horizontal relative to the force of gravity;
second means for rotatably securing the arm to said first means for rotation about a second axis normal to and intersecting said first axis; and
a carrier having first and second spaced ends, said carrier being secured to the arm for supporting at the first carrier end an X-ray source and at the second carrier end an X-ray detector opposite the X-ray source and third means for rotatably securing the carrier to said arm for rotation about a third axis parallel to and spaced from the second axis.

10. The apparatus of claim 9 wherein said detector and source define an X-ray beam fourth axis, said fourth axis being normal to said third axis.

11. The apparatus of claim 9 wherein said third and fourth axes are at a region spaced from the intersection of said second and third axes.

12. An X-ray examination apparatus, comprising a column extending in a given direction parallel to the force of gravity, an arm connected to said column and rotatable about a horizontal axis relative to gravity and to which arm there is coupled a carrier which supports at a first end an X-ray source and at a second end an X-ray detector which is arranged opposite the X-ray source, the combination therewith comprising means for rotatably securing the arm to said column for rotation about said horizontal axis and about a second axis rotatable about the horizontal axis, said axes being orthogonal and intersecting, said horizontal axis being normal to said given direction, and a counterweight secured to the arm at one side, the arm, the carrier, the X-ray source, the X-ray detector and the counterweight having a common center of gravity substantially coincident with the point of intersection of the intersecting axes.

* * * * *